| United States Patent [19] | [11] Patent Number: 5,003,072 |
| Partis et al. | [45] Date of Patent: Mar. 26, 1991 |

[54] 1,5-DIDEOXY-1,5-IMINO-D-GLUCITOL DERIVATIVES

[75] Inventors: Richard A. Partis, Evanston; Francis J. Koszyk, Chicago; Richard A. Mueller, Glencoe, all of Ill.

[73] Assignee: G. D. Searle & Co., Skokie, Ill.

[21] Appl. No.: 418,091

[22] Filed: Oct. 12, 1989

Related U.S. Application Data

[63] Continuation-in-part of Ser. No. 266,767, Nov. 3, 1988, abandoned.

[51] Int. Cl.$^5$ ............................................. C07D 213/69
[52] U.S. Cl. .................................... 546/243; 546/116; 546/193; 546/220; 546/243; 514/885
[58] Field of Search ............... 546/242, 220, 193, 116, 546/243; 514/315, 318, 328

[56] References Cited

U.S. PATENT DOCUMENTS

| 4,182,767 | 1/1980 | Murai et al. ................. 546/242 X |
| 4,348,402 | 9/1982 | Kinast et al. .................. 546/242 X |
| 4,639,436 | 1/1987 | Junge et al. ......................... 514/24 |
| 4,849,430 | 7/1989 | Fleet et al. ........................ 514/315 |

FOREIGN PATENT DOCUMENTS

WO87/03903  7/1987  PCT Int'l Appl. .

OTHER PUBLICATIONS

Frank et al., *Antimicrob. Agents Chemother.* 31, 1369–1374 (1987).
Sunkara et al., *Soc. Complex Carbohyd.* 17th Ann. Meet., San Antonio, Nov. 3–5, 1988 Abst. 9.
*Chem. Abst.* 86: 167851r (1977).
*Chem. Abst.* 68: 78526Z (1968).
*Chem. Abst.* 67: 3207s (1967).
*Chem. Abst.* 92: 76884m (1980).
*Chem. Abst.* 84: 44569f (1976).

*Primary Examiner*—Robert W. Ramsuer
*Assistant Examiner*—Jacqueline Haley
*Attorney, Agent, or Firm*—Scott J. Meyer; James W. Williams, Jr.

[57] ABSTRACT

O-acylated derivatives of 1,5-dideoxy-1,5-imino-D-glucitol and their N-alkyl, N-acyl and N-aryl derivatives in which from one to four of the free hydroxyl groups are acylated with acyl groups having from one to eight carbon atoms and in which the N-alkyl and N-acyl substituents contain from four to fourteen carbon atoms and the N-aryl substituents contain from seven to fourteen carbon atoms are disclosed, provided that when N-aryl is benzyloxycarbonyl, the O-acyl groups contain four to eight carbon atoms.

4 Claims, No Drawings

1,5-DIDEOXY-1,5-IMINO-D-GLUCITOL DERIVATIVES

CROSS-REFERENCE TO RELATED APPLICATION

This is a continuation-in-part of application Ser. No. 07/266,767, filed Nov. 3, 1988, now abandoned.

BACKGROUND OF THE INVENTION

This invention relates to novel antiviral compounds and, more particularly, to O-acylated derivatives of 1,5-dideoxy-1,5-imino-D-glucitol and their N-alkyl, N-acyl and N-aryl derivatives. These compounds are inhibitors of visna virus, a pathogenic virus for sheep and goats. These antiviral compounds also have potential use for the treatment of acquired immune deficiency syndrome (AIDS) and AIDS-related complex (ARC).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+ T-cells (or CD4+ cells). See, e.g., Gallo et al., Science 224, 500–503 (1984), and Popovic et al., Ibid., 497–500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [*Ann. Virol. Inst. Pasteur* 135 E, 119–134 (1984)], while HIV-2 was more recently isolated by Montagnier and his coworkers in 1986 [*Nature* 326, 662–669 (1987)]. As used herein, HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, *Science* 241, 426–432 (1988).

The first drug to be approved by the U.S. Food and Drug Administration (FDA) for treatment of AIDS was zidovudine, better known under its former name, azidothymidine (AZT). Chemically, this drug is 3'-azido-3'-deoxythymidine. This drug was originally selected as a potential weapon against AIDS because it was shown to inhibit replication of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

The HIV inhibitory activity of 1,5-dideoxy-1,5-imino-D-glucitol (deoxynojirimycin) and its N-methyl derivative is disclosed in PCT Inter. Appln. No. 87/03903, published July 2, 1987. The substantially more effective anti-HIV activity of the N-butyl derivative of deoxynojirimycin is disclosed in U.S. Pat. No. 4,849,430.

U.S. Pat. Nos. 4,182,767 and 4,639,436 show the syntheses and antihyperglycemic use of N-alkyl derivatives of deoxynojirimycin. These patents suggest the use of acyl blocking groups or hydroxylprotective groups in the syntheses of the desired antihyperglycemic products. However, these blocking groups are proposed only for the preparation of the intermediates and are removed with no isolation or characterization of compounds for antiviral use.

BRIEF DESCRIPTION OF THE INVENTION

In accordance with the present invention O-acylated derivatives of 1,5-dideoxy-1,5-imino-D-glucitol and their N-alkyl, N-acyl, and N-aryl derivatives are provided which have useful antiviral activity against lentiviruses.

1,5-dideoxy-1,5-imino-D-glucitol is a six-membered heterocyclic compound having nitrogen in the ring and four hydroxyl groups. It is thus described by a systematic chemical name as a sugar derivative in which the six-membered ring is considered as a mimic of pyranose, with nitrogen instead of oxygen in the ring. It can also be described structurally as a derivative of piperidine. As defined herein, at least one and preferably all the free hydroxyl groups on 1,5-dideoxy-1,5-imino-D-glucitol and the N-substituted derivatives are acylated with acyl groups having from one to eight carbon atoms; provided that when N-aryl is benzyloxycarbonyl, the O-acyl groups contain four to eight carbon atoms. These compounds thus will contain from 1 to 4 such acyl groups. In the N-alkyl and N-acyl derivatives, the N-alkyl and N-acyl groups contain from 4 to 14 carbon atoms and preferably from 4 to 9 carbon atoms. In the N-aryl derivatives, the N-aryl substituents contain from 7 to 14 carbon atoms.

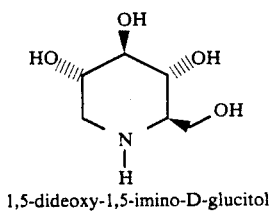

1,5-dideoxy-1,5-imino-D-glucitol

The N-alkyl groups are illustrated, e.g., by butyl, pentyl, hexyl, nonyl, 2-ethylbutyl and 2-methylpentyl.

The N-acyl groups are illustrated, e.g., by methyl malonyl and ethyl malonyl.

The N-aryl groups are illustrated, e.g., by phenylacetyl, benzyloxycarbonyl, benzoyl, biphenylacetyl, phenoxyacetyl, chlorophenylacetyl, hydrocinnamoyl, cinnamoyl and nicotinoyl.

The aryl groups can have one or more, preferably 1 to 3, identical or different substituents. Examples of substituents are alkyl or alkoxy having from one to six carbon atoms; halogen such as Cl, Br or F; and hydroxyl.

Illustrative examples of the antiviral O-acylated derivatives of 1,5-dideoxy-1,5-imino-D-glucitol and their N-alkyl, N-acyl and N-aryl derivatives are the following:

1,5-(Benzyloxycarbonylimino)-1,5-dideoxy-D-glucitol, tetraacetate, 1,5-(Phenylacetylimino)-1,5-dideoxy-D-glucitol, tetraacetate,
1,5-(Benzoylimino)-1,5-dideoxy-D-glucitol, tetraacetate,
1,5-(Butylimino)-1,5-dideoxy-D-glucitol, tetraacetate,
1,5-(Ethyl malonylimino)-1,5-dideoxy-D-glucitol, tetraacetate,
1,5-(Hexylimino)-1,5-dideoxy-D-glucitol, tetraacetate,
1,5-(Nonylimino)-1,5-dideoxy-D-glucitol, tetraacetate,
1,5-(Benzyloxycarbonylimino)-1,5-dideoxy-D-glucitol, tetraisobutyrate,
1,5-(Butylimino)-1,5-dideoxy-D-glucitol, tetrabutyrate,
1,5-(Butylimino)-1,5-dideoxy-D-glucitol, tetrapropionate,
1,5-(Butylimino)-1,5-dideoxy-D-glucitol, tetrabenzoate,
1,5-Dideoxy-1,5-imino-D-glucitol, tetraisobutyrate,
1,5-(Hydrocinnamoylimino)-1,5-dideoxy-D-glucitol, tetraacetate,
1,5-(Methyl malonylimino)-1,5-dideoxy-D-glucitol, tetraacetate,
1,5-(Butylimino)-1,5-dideoxy-D-glucitol, tetraisobutyrate,
1,5-(Butylimino)-1,5-dideoxy-4R,6-O-(phenylmethylene)-D-glucitol, diacetate,
1,5-[(Phenoxymethyl)carbonylimino]-1,5-dideoxy-D-glucitol, tetraacetate,
1,5-[(Ethylbutyl)imino]-1,5-dideoxy-D-glucitol, tetraacetate,
1,5-(Butylimino)-1,5-dideoxy-D-glucitol, 2,3-diacetate,
1,5-(Hexylimino)-1,5-dideoxy-4R,6-O-(phenylmethylene)-D-glucitol, diacetate,
1,5-(Hexylimino)-1,5-dideoxy-D-glucitol, 2,3-diacetate,
1,5-[(2-Methylpentyl)imino]-1,5-dideoxy-D-glucitol, tetraacetate,
1,5-(Butylimino)-1,5-dideoxy-D-glucitol, 6-acetate,
1,5-[(3-Nicotinoyl)imino]-1,5-dideoxy-D-glucitol, tetraacetate,
1,5-(Cinnamoylimino)-1,5-dideoxy-D-glucitol, tetraacetate,
1,5-(Butylimino)-1,5-dideoxy-D-glucitol, 2,3-dibutyrate,
1,5-(Butylimino)-1,5-dideoxy-4R,6-O-(phenylmethylene)-D-glucitol, 2,3-dibutyrate
1,5-(Phenylacetylimino)-1,5-dideoxy-D-glucitol, tetraisobutyrate,
1,5-[(4-Chlorophenyl)acetylimino]-1,5-dideoxy-D-glucitol, tetraacetate,
1,5-[(4-Biphenyl)acetylimino]-1,5-dideoxy-D-glucitol, tetraacetate,
1,5-(Benzyloxycarbonylimino)-1,5-dideoxy-D-glucitol, tetrabutyrate, and
1,5-Dideoxy-1,5-imino-D-glucitol, tetrabutyrate.

These novel antiviral compounds can be prepared from the amine, 1,5-dideoxy-1,5-imino-D-glucitol, by conventional N-alkylation or N-acylation with appropriate alkyl, acyl or aryl groups. The free hydroxyl groups on the amine can be acylated either before or after this N-alkylation or N-acylation.

In preferred embodiments alkylation can be carried out by reaction of the starting amine with an appropriate alkylaldehyde or an appropriate arylaldehyde. Illustrative alkylaldehydes are butyraldehyde, ethylbutyraldehyde, 2-methylvaleraldehyde, caproaldehyde, and nonylaldehyde. Illustrative arylaldehydes are, e.g., benzaldehyde, ethylbenzaldehyde and hydrocinnamaldehyde.

Alternatively, reaction of the starting amine with benzyl chloroformate can be carried out to give N-benzyloxycarbonyl derivatives of the amine.

Acylation of the free hydroxyl groups is conveniently carried out by reaction of the amine with an appropriate acid anhydride such as, e.g., the acetic-, propionic-, butyric-, isobutyric- and benzoic anhydrides.

In other preferred embodiments, the pre-acylated amine can be reacted with alkylating or acylating agents to form the N-alkyl, N-acyl and N-aryl derivatives. Illustrative of such alkylating agents are, e.g., benzoyl chloride or phenylacetic anhydride together with triethylamine. Illustrative of such acylating agents are methyl malonyl chloride and ethyl malonyl chloride.

Although specific methods of production are described herein, it will be appreciated that the novel antiviral compounds claimed herein are not limited to any particular method of production.

The foregoing compounds can be demonstrated to have inhibitory activity against visna virus in a conventional plaque reduction assay. Visna virus, a lentivirus genetically very similar to the AIDS virus, is pathogenic for sheep and goats. See Sonigo et al., *Cell* 42, 369-382 (1985); Haase, *Nature* 322, 130-136 (1986). Inhibition of visna virus replication in vitro as a useful model for human immunodeficiency virus (HIV) and its inhibition by test compounds has been described by Frank et al., *Antimicrobial Agents and Chemotherapy* 31 (9), 1369-1374 (1987). The N-butyl derivative of 1,5-dideoxy-1,5-imino-D-glucitol, also referred to as n-butyl-deoxynojirimycin (N-Bu-DNJ), was used as a control standard for comparison with various novel compounds of this invention. The HIV inhibitory activity of N-Bu-DNJ is described in U.S. Pat. No. 4,849,430.

Inhibitory activity can also be demonstrated by the acylated derivatives against alpha- and beta-glucosidase enzymes. In some cases, the non-acylated derivatives also have effective inhibitory activity against visna virus, cytomegalovirus (CMV) and/or the alpha- and beta-glucosidases.

DETAILED DESCRIPTION OF THE INVENTION

The following detailed examples will further illustrate the invention although it will be understood that the invention is not limited to these specific examples.

EXAMPLE 1

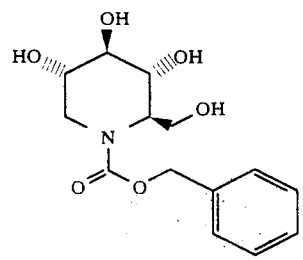

1,5-(Benzyoxycarbonylimino)-1,5-dideoxy-D-glucitol

Benzyl chloroformate (1.15 g, 0.00674 mole was added to a solution of 1,5-dideoxy-1,5-imino-D-glucitol (1.0 g, 0.00613 mole), in 50 ml saturated aqueous sodium hydrogen carbonate and stirred for 20 hrs. at room temperature. The product was extracted into ethyl acetate (3×75 ml), dried over anhydrous sodium sulfate, filtered and concentrated in vacuo to an oil. Chromatography on silical gel gave the title compound (1.2 g). Structure assignment was supported by NMR and infrared spectra and by elemental analysis. Analysis calcd. for $C_{14}H_{19}NO_6$: C, 56.56; H, 6.44; N, 4.71. Found: C, 56.29; H, 6.62; N, 4.53.

EXAMPLE 2

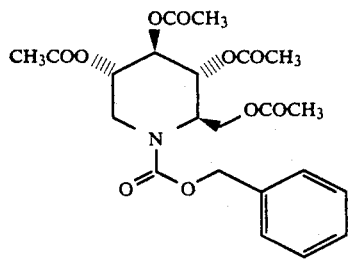

1,5-(Benzyloxycarbonylimino)-1,5-dideoxy-D-glucitol, tetraacetate

To a solution of the title product of Example 1 (491 mg, 1.65 moles) in 5 ml of pyridine was added 2 ml of acetic anhydride. The resulting mixture was stirred for 15 minutes at room temperature and then at reflux for 5 minutes. After cooling, the mixture was poured into 25 ml of ice water and extracted with three portions of ethyl acetate. The combined organic extracts were washed with dilute hydrochloric acid, dried over sodium sulfate, filtered, and the solvent removed on a rotary evaporator. Chromatograghy on silica gel using a gradient of 25 to 100% ethyl acetate-hexane as eluant gave the title compound (510 mg) as an oil. Analysis for $C_{22}H_{27}NO_{10}$ (MW 465.46): Calcd. C, 56.76; H, 5.85; N, 3.01. Found: C, 56.72; H, 5.82; N, 3.02.

EXAMPLE 3

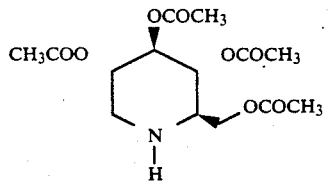

1,5-Dideoxy-1,5-imino-D-glucitol, tetraacetate

The title compound of Example 2 (13.417 g, 0.029 moles) was hydrogenated (5 psi, room temperature 2 hrs.) in 250 ml of methanol containing 4% Pd/C (3.0 g). This mixture was filtered and concentrated in vacuo to give an oil. Chromatography on silica gel gave the title compound as a waxy solid. Structure assignment was supported by NMR, infrared spectra and elemental analysis. Analysis calcd. for $C_{14}H_{21}NO_8$: C, 50.75; H, 6.39; N, 4.23. Found: C, 50.53; H, 6.41; N, 4.14.

EXAMPLE 4

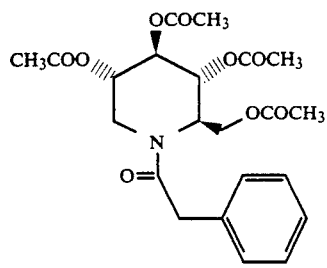

1,5-(Phenylacetylimino)-1,5-dideoxy-D-glucitol-tetraacetate

Phenylacetyl chloride (0.23 g, 0.0015 mole) was added to a cold (−76° C., solution of the title compound of Example 3 (0.5 g, 0.0015 mole) in 30 ml tetrahydrofuran. Triethylamine (0.5 ml) was added and the solution stirred for 20 hrs at room temperature. Triethylamine hydrochloride was removed by filtration and the filtrate concentrated in vacuo to give 0.81 g of an oil. Chromatography on silica gel and recrystallizing from ethyl acetate/hexane gave the title product, m.p. 98°–100° C. Structure assignment was supported by NMR, infrared spectra and elemental analysis. Analysis calcd. for $C_{22}H_{27}NO_9$: C, 58.79; H, 6.05; N, 3.12. Found: C, 58.74; H, 6.12; N, 3.14.

EXAMPLE 5

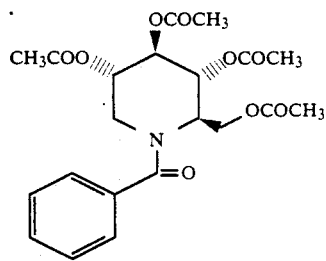

1,5-(Benzoylimino)-1,5-dideoxy-D-glucitol, tetraacetate

The title compound, m.p. ca. 138° C., was prepared by the method of Example 4 using benzoyl chloride instead of phenylacetyl chloride. Structure assignment was supported by NMR, infrared spectra and elemental analysis. Analysis calcd. for $C_{21}H_{25}NO_9$: C, 57.93; H 5.79; N, 3.22. Found: C, 57.88; H, 5.82; N, 3.30.

EXAMPLE 6

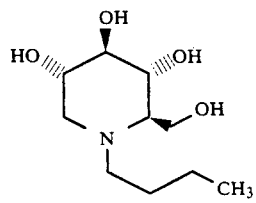

1,5-(Butylimino)-1,5-dideoxy-D-glucitol

A solution of 1,5-dideoxy-1,5-imino-D-glucitol (5.14 g, 0.0315 mole), butyraldehyde (3.35 ml, 0.0380 mole) and Pd black (1 g) in 200 ml methanol was hydrogenated (60 psi/29° C./21 hrs.). After filtering the resulting mixture, the filtrate was concentrated in vacuo to an oil. The title compound was crystallized from acetone and recrystallized from methanol/acetone, m.p. ca. 132° C. Structure assignment was supported by NMR, infrared spectra and elemental analysis. Analysis calcd. for $C_{10}H_{21}NO_4$: C, 54.78; H, 9.65; N, 6.39. Found: C, 54.46; H, 9.33; N, 6.46.

EXAMPLE 7

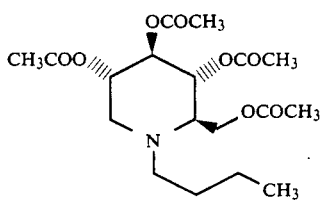

1,5-(Butylimino)-1,5-dideoxy-D-glucitol, tetraacetate

Acetic anhydride (1.08 g, 0.0106 mole) was added to the title compound of Example 6 (0.50 g, 0.0023 mole) in 5 ml pyridine and stirred for 17 days at room temperature. The product was evaporated under nitrogen gas. The resulting title compound was purified by silica gel chromatography. Structure assignment was supported by NMR, infrared spectra and elemental analysis. Analysis calcd. for $C_{18}H_{29}NO_8$: C, 55.80; H, 7.54; N, 3.62. Found: C, 55.42; H, 7.50; N, 3.72.

EXAMPLE 8

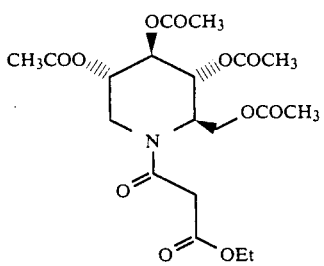

1,5-(Ethyl malonylimino)-1,5-dideoxy-D-glucitol, tetraacetate

Ethyl malonyl chloride (0.5 g, 0.0033 mole) in 10 ml tetrahydrofuran was added to a cold (0° C.) solution of the title compound of Example 3 (1.0 g, 0.0030 mole) in 30 ml tetrahydrofuran. After stirring for 30 min. a solution of triethylamine (0.67 g, 0.0066 mole) in 10 ml tetrahydrofuran was added. The mixture was allowed to come to room temperature and stirred for 20 hrs. Triethylamine hydrochloride was removed by filtration and the filtrate concentrated in vacuo to give an oil. Chromatography on silica gel gave the title compound as a clear oil. Structure assignment was supported by NMR, infrared spectra and elemental analysis. Analysis calcd. for $C_{19}H_{27}NO_{11}$: C, 51.23; H, 6.11; N, 3.14. Found: C, 50.99; H, 6.14; N, 3.13.

EXAMPLE 9

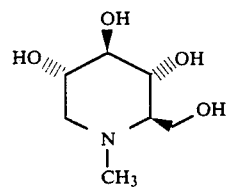

1,5-(Methylimino)-1,5-dideoxy-D-glucitol

A solution of 1,5-dideoxy-1,5-imino-D-glucitol (7.5 g, 0.046 mole), formaldehyde (37%, 26.0 g, 0.322 mole) and 5% Palladium black in 300 ml methanol was hydrogenated (60 psi/25° C./20 hrs). After filtering the resulting mixture, the filtrate was concentrated to give a foam. The product was crystallized from methanol-acetone to give a white solid. Structure assignment was supported by NMR, infrared spectra and elemental analysis. Analysis calcd. for $C_7H_{15}NO_4$, C 47.45; H, 8.53; N, 7.91. Found: C, 47.24; H, 8.66; N, 7.83.

EXAMPLE 10

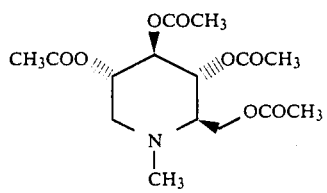

1,5-(Methylimino)-1,5-dideoxy-D-glucitol, tetraacetate

Acetic anhydride (0.69 g, 0.0068 mole) was added to the title compound of Example 9 (0.20 g, 0.0011 mole) in 10 ml pyridine and stirred at room temperature for 5 days. The product was concentrated with a gentle flow of nitrogen gas. The residue was dissolved in 25 ml ethyl acetate, washed with water, dried over sodium sulfate, filtered and concentrated to an oil. The product was purified by silica gel chromatography and recrystallized from ethyl acetate-hexane (m.p. 102° C.). Structure assignment was supported by NMR, infrared spectra and elemental analysis. Analysis calcd. for $C_{15}H_{23}NO_8$: C, 52.17; H, 6.71; N, 4.06. Found: C, 52.15; H, 6.72; N, 3.97.

EXAMPLE 11

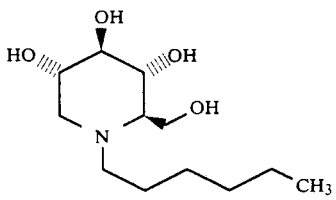

1,5-(Hexylimino)-1,5-dideoxy-D-glucitol

A mixture of 1,5-dideoxy-1,5-imino-D-glucitol (0.5 g, 0.0031 moles), caproaldehyde (0.45 g, 0.0045 mole) and 5% Palladium black (0.1 g) in methanol (105 ml) was hydrogenated (5 psi/25° C./5 days). After filtering the resulting mixture, the filtrate was concentrated with a flow of nitrogen to give an oily solid. The title compound was crystallized from acetone-ethanol, DSC ca. 115° C. Structure assignment was supported by NMR, infrared spectra and elemental analysis. Analysis calcd. for $C_{12}H_{25}NO_4$: C, 58.27; H, 10.19; N, ; 5.66. Found: C, 58.19; H, 10.24; N, 5.65.

EXAMPLE 12

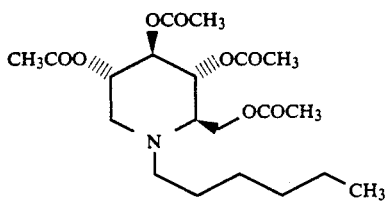

1,5-(Hexylimino)-1,5-dideoxy-D-glucitol, tetraacetate

The title compound was prepared by the Method of Example 10 utilizing the product of Example 11 instead of 1,5-(methylimino)-1,5-dideoxy-D-glucitol. The structure assignment was supported by NMR, infrared spectra and elemental analysis. Analysis calcd. for $C_{20}H_{33}NO_8$: C, 57.82; H, 8.01; N, 3.37. Found: C, 57.73; H, 7.83; N, 3.36.

EXAMPLE 13

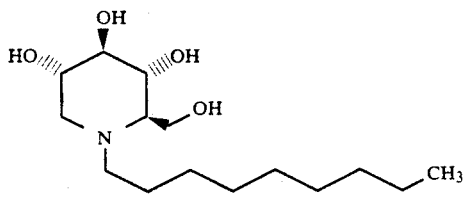

1,5-(Nonylimino)-1,5-dideoxy-D-glucitol

A solution of 1,5-dideoxy-1,5-imino-D-glucitol (0.5 g, 0.0031 mole); nonyl aldehyde (0.52 g, 0.0037 mole) and 5% Pd black (0.1 g) in methanol (100 ml) was hydrogenated (60 psi/25° C./46 hrs.). After filtering the resulting mixture, the filtrate was concentrated with a gentle flow of nitrogen to an oily solid. This material was stirred with a small amount of acetone and the solid filtered. Recrystallization from ethanol-acetone gave the title compound, DSC ca. 109° C. Structure assignment was supported by NMR, infrared spectra and elemental analysis. Analysis calcd. for $C_{15}H_{31}NO_4$: C, 62.25; H, 10.80; N, 4.84. Found: C, 62.15; H, 10.86; N, 4.79.

EXAMPLE 14

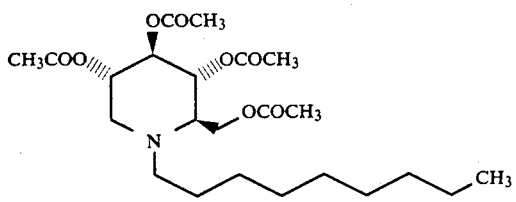

1,5-(Nonylimino)-1,5-dideoxy-D-glucitol, tetraacetate

The title compound was prepared by the Method of Example 10 utilizing the product of Example 13 instead of 1,5-(methylimino)-1,5-dideoxy-D-glucitol. The structure assignment was supported by NMR, infrared spectra and elemental analysis. Analysis calcd. for $C_{23}H_{39}NO_8$: C, 60.37; H, 8.59; N, 3.06. Found: C, 60.19; H, 7.99; N, 3.12.

EXAMPLE 15

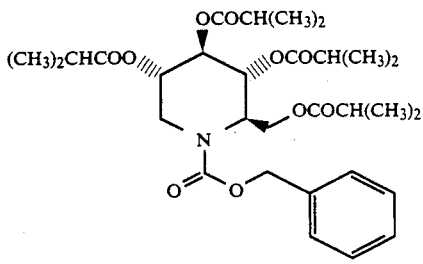

1,5-(Benzyloxlycarbonylimino)-1,5-dideoxy-D-glucitol, tetraisobutyrate

To a solution of the title product of Example 1 (2.0 g, 0.0067 mole) in 30 ml pyridine was added isobutyric anhydride (6.4 g, 0.0436 mole) and stirred at room temperature for 6 days. The reaction was poured into 150 ml water, stirred for 20 hrs. and extracted with two portions of ethyl acetate (2×100 ml). The combined organic extracts were washed with water (4×75 ml), dried over sodium sulfate, filtered, and the solvent removed on a rotary evaporator to give an oil. The title compound was purified by silica gel chromatography. The structure assignment was supported by NMR, infrared spectra and elemental analysis. Analysis calcd. for $C_{30}H_{43}NO_{10}$: C, 62.38; H, 7.50; N, 2.42. Found: C, 62.23; H, 7.60; N, 2.44.

EXAMPLE 16

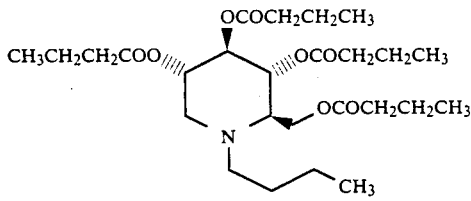

1,5-(Butylimino)-1,5-dideoxy-D-glucitol, tetrabutyrate

The title compound was prepared by the Method of Example 7 using n-butyric anhydride instead of acetic anhydride. After purification by silica gel chromatography the product was crystallized from pentane. The structure assignment was supported by NMR, infrared spectra and elemental analysis. Analysis calcd. for $C_{22}H_{45}NO_8$: C, 62.50; H, 9.08; N, 2.80. Found: C, 62.48; H, 9.12; N, 2.84.

EXAMPLE 17

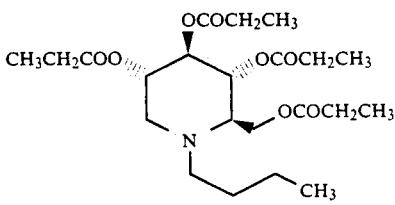

1,5-(Butylimino)-1,5-dideoxy-D-glucitol, tetrapropionate

The title compound was prepared by the Method of Example 7 substituting propionic anhydride for acetic anhydride. The structure was supported by NMR, infrared spectra and elemental analysis. Analysis calcd. for $C_{22}H_{37}NO_8$: C, 59.58; H, 8.41; N, 3.16. Found: C, 59.56; H, 8.68; N, 3.19.

EXAMPLE 18

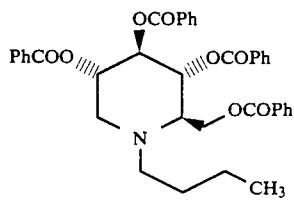

1,5-(Butylimino)-1,5-dideoxy-D-glucitol, tetrabenzoate

The title compound was prepared by the Method of Example 7 substituting benzoic anhydride for acetic anhydride. The reaction was allowed to stir at room temperature for 27 days. The structure assignment was supported by NMR, infrared spectra and elemental analysis. Analysis calcd. for $C_{38}H_{37}NO_8$: C, 71.80; H, 5.87; N, 2.20. Found: C, 71.49; H, 5.92; N, 2.24.

EXAMPLE 19

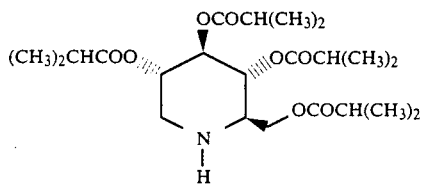

1,5-Dideoxy-1,5-imino-D-glucitol, tetraisobutyrate

The title compound of Example 15 (2.65 g, 0.0046 mole) was hydrogenated (15 psi, room temperature, 4 hr.) in 100 ml methanol containing 5% Pd/C. This mixture was filtered and concentrated by a rotary evaporator to a solid which was recrystallized from ethyl acetate-hexane (DSC 63° C.). Assignment was supported by NMR, infrared spectra and elemental analysis. Analysis calcd. for $C_{22}H_{37}NO_8$: C, 59.58; H, 8.41; N, 3.16. Found: C, 59.49; H, 8.46; N, 3.17.

EXAMPLE 20

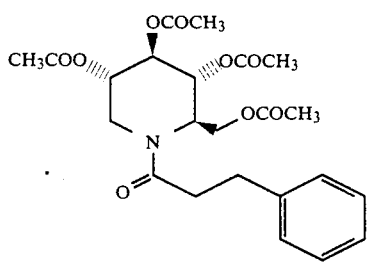

1,5-(Hydrocinnamoylimino)-1,5-dideoxy-D-glucitol, tetraacetate

By the method of Example 4 and substituting hydrocinnamoyl chloride for phenylacetyl chloride the title compound was prepared Structure assignment was supported by NMR, infrared spectra and elemental analysis. Analysis calcd. for $C_{23}H_{29}NO_9$: C, 59.60; H, 6.31; N, 3.02. Found: C, 59.49; H, 6.25; N, 3.08.

EXAMPLE 21

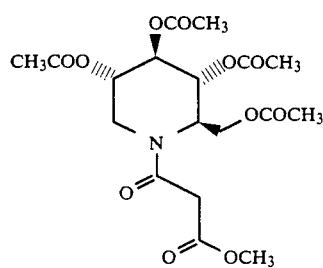

1,5-(Methyl malonylimino)-1,5-dideoxy-D-glucitol, tetraacetate

The title compound was prepared by the Method of Example 8 and substituting methyl malonyl chloride for ethyl malonyl chloride. The structure assignment was supported by NMR, infrared spectra and elemental analysis. Analysis calcd. for $C_{18}H_{25}NO_{11}$: C, 50.12; H, 5.84; N, 3.25. Found: C, 49.91; H, 5.82; N, 3.13.

EXAMPLE 22

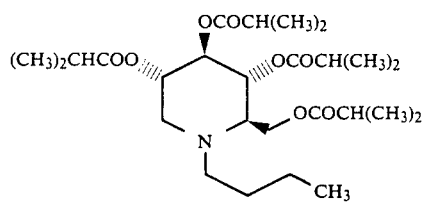

1,5-(Butylimino)-1,5-dideoxy-D-glucitol, tetraisobutyrate

The title compound was prepared by the Method of Example 7 and substituting isobutyric anhydride for acetic anhydride, m.p. 59° C. The structure was supported by NMR, infrared spectra and elemental analysis. Analysis calcd. for $C_{26}H_{45}NO_8$: C, 62.50; H, 9.08; N, 2.80. Found: C, 62.43; H, 9.24; N, 2.82.

EXAMPLE 23

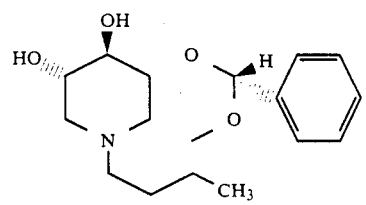

1,5-(Butylimino)-1,5-dideoxy-4R,6-O-(phenylmethylene)-D-glucitol p-Toluenesulfonic acid monohydrate (10.4 g, 0.055 mole) was added to a solution of dimethoxytoluene (20.8 g, 0.137 mole) in 150 ml of dimethylformamide. After stirring for 3.5 hrs, 1,5-(butylimino)-1,5-dideoxy-D-glucitol (10.0 g, 0.046 mole) was added and the solution was stirred at room temperature for 18 days. The reaction was concentrated on a rotary evaporator. The residue was passed through a column containing Amberlite IRA-400 ion exchange resin with methanol. The eluant was concentrated to a brown oil. The title compound was purified by silica gel chromatography and crystallized from ethyl acetate-hexane (DSC 118° C.). The structure assignment was supported by NMR, infrared spectra and elemental analysis. Analysis calcd. for $C_{17}H_{25}NO_4$: C, 66.43; H, 8.20; N 4.56. Found: C, 66.38; H, 8.20; N, 4.52.

EXAMPLE 24

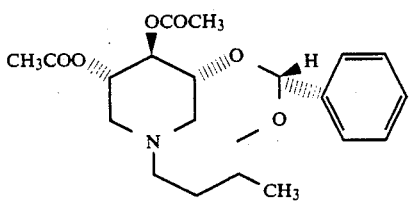

1,5-(Butylimino)-1,5-dideoxy-4R,6-O-(phenylmethylene)-D-glucitol, diacetate

Acetic anhydride (0.30 g, 0.0029 mole) was added to the product of Example 23 (0.30 g, 0.001 mole) in 10 ml pyridine and stirred for 5 days at room temperature. Water (5 ml) was added and the solution stirred for 1 hr. After removal of the solvent by a rotary evaporator, the product was purified by silica gel chromatography and recrystallized from ethyl acetate-hexane (DSC 126° C.). Structure assignment was supported by NMR, infrared spectra and elemental analysis. Analysis calcd. for $C_{21}H_{29}NO_6$: C, 64.43; H, 7.47; N, 3.58. Found: C, 64.39; H, 7.70; N, 3.53.

EXAMPLE 25

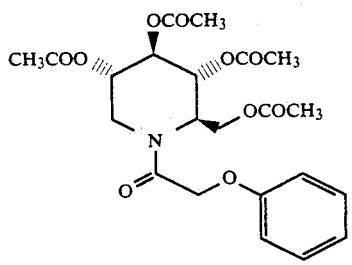

1,5-[(Phenoxymethyl)carbonylimino]-1,5-dideoxy-D-glucitol, tetraacetate

The title compound was prepared by the Method of Example 4 and substituting phenoxyacetyl chloride for phenylacetyl chloride (DSC, 219° C.). Structure assignment was supported by NMR, infrared spectra and elemental analysis. Analysis calcd. for $C_{22}H_{27}NO_{10}$: C, 56.77; H, 5.85; N, 3.01. Found: C, 56.81; H, 5.83; N, 3.21.

EXAMPLE 26

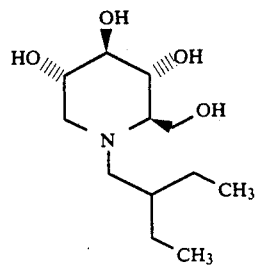

1,5-[(2-Ethylbutyl)imino]-1,5-dideoxy-D-glucitol

A solution of 1,5-dideoxy-1,5-imino-D-glucitol (0.99 g, 0.0061 mole), 2-ethylbutyraldehyde (0.98 g, 0.0098 mole) and 5% Pd black in methanol (68 ml), tetrahydrofuran (34 ml) and water (17 ml) was hydrogenated (5 psi/25° C./72 hrs.). After filtering the resulting mixture, the filtrate was concentrated to an oily solid. This residue was dissolved in methanol (40 ml) and cooled. The white solid was removed by filtration to give as 1,5-dideoxy-1,5-imino-D-glucitol. The filtrate was concentrated to an oil. The product was purified by silica gel chromatography to give a white solid. Recrystallization from methanol-ethyl acetate gave the title compound, DSC ca. 95° C. Structural assignment was supported by NMR, infrared spectra and elemental analysis. Analysis calcd. for $C_{12}H_{25}NO_4$: C, 58.27; H, 10.19; N, 5.66. Found: C, 57.89; H, 10.09; N, 5.69.

EXAMPLE 27

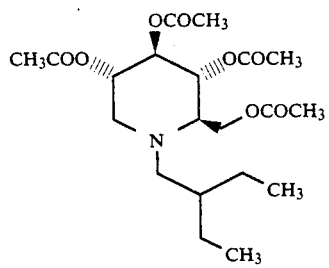

1,5-[(2-Ethylbutyl)imino]-1,5-dideoxy-D-glucitol, tetraacetate

The title compound was prepared by the Method of Example 7 and substituting 1,5-[(2-ethylbutyl)imino]-1,5-dideoxy-D-glucitol for 1,5-(butylimino)-1,5-dideoxy-D-glucitol. Structure assignment was supported by NMR, infrared spectra and elemental analysis. Analysis calcd. for $C_{20}H_{33}NO_8$: C, 57.82; H, 8.01; N, 3.37. Found: C, 57.42; H, 7.92; N, 3.31.

EXAMPLE 28

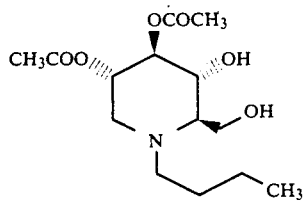

1,5-(Butylimino)-1,5-dideoxy-D-glucitol, 2,3-diacetate

A mixture of the title compound of Example 24 (1.9 g, 0.0049 mole) and 20% Pd black (2.0 g) in methanol, tetrahydrofuran and methanol (6:4:2) was hydrogenated (60 psi/60° C./21 hr.). After filtering the resulting mixture, the filtrate was concentrated in vacuo to an oil. The product was purified by silica gel chromatography. Structure assignment was supported by NMR and elemental analysis. Analysis calcd. for $C_{14}H_{25}NO_6$: C, 55.43; H, 8.31; N, 4.62. Found: C, 55.40; H, 8.38; N, 4.50.

EXAMPLE 29

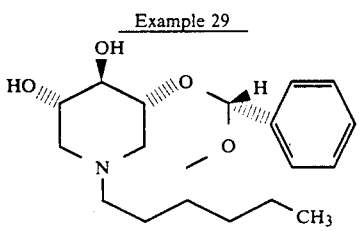

1,5-(Hexylimino)-1,5-dideoxy-4R,6-O-(phenylmethylene)-D-glucitol

The title compound was prepared by the Method of Example 23 and substituting the product of Example 11 for 1,5-(butylimino)-1,5-dideoxy-D-glucitol (DSC 101° C.) Structure assignment was supported by NMR, infrared spectra and elemental analysis. Analysis calcd. for $C_{19}H_{29}NO_4$: C, 68.03; H, 8.71; N, 4.18. Found: C, 68.04; H, 8.76; N, 4.15.

EXAMPLE 30

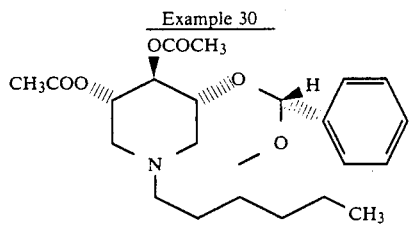

1,5-(Hexylimino)-1,5-dideoxy-4R,6-O-(phenylmethylene)-D-glucitol, 2,3-diacetate

The title compound can be prepared by the Method of Example 24 and substituting the product of Example 29 for the product of Example 23.

EXAMPLE 31

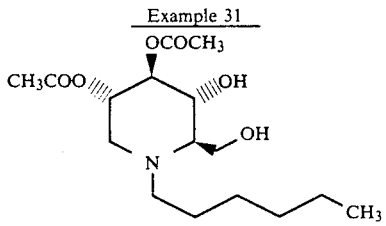

1,5-(Hexylimino)-1,5-dideoxy-D-glucitol, 2,3-diacetate

The title compound can be prepared by the Method of Example 28 by substituting the product of Example 30 for the product of Example 24 in the synthesis reaction.

EXAMPLE 32

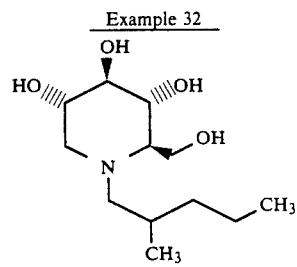

1,5-[(2-Methylpentyl)imino]-1,5-dideoxy-D-glucitol

The title compound was prepared as a solid by the Method of Example 26 by using 2-methylvaleraldehyde instead of 2-ethylbutyraldehyde in the synthesis reaction. (DSC ca. 89° C.) The structure was supported by NMR; infrared spectra and mass spectroscopy.

EXAMPLE 33

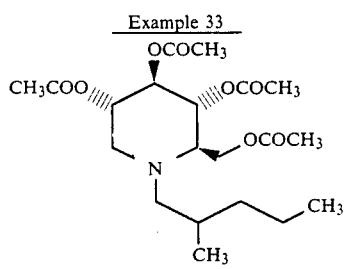

1,5-[(2-Methylpentyl)imino]-1,5-dideoxy-D-glucitol, tetraacetate

The title compound was prepared by the Method of Example 7 by substituting 1,5-[(2-Methylpentyl)imino]-1,5-dideoxy-D-glucitol for 1,5-(butylimino)-1,5-dideoxy-D-glucitol in the synthesis reaction. The structure assignment was supported by CMR and NMR.

EXAMPLE 34

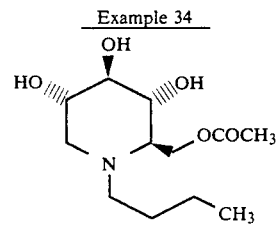

1,5-(Butylimino)-1,5-dideoxy-D-glucitol, 6-acetate

Acetic anhydride (0.46 g, 0.0046 mole) was added to the title compound of Example 6 (1.0 g, 0.0046 mole) in 150 ml pyridine cooled to −40° C. by a dry ice/acetone bath. The reaction was allowed to come to room temperature and stirred for 20 hrs. Water (5 ml) was added and the reaction stirred for 1 hr. The solution was concentrated in vacuo to an oil. The title compound was purified by silica gel chromatography to give a solid which was recrystallized from methanol-ethyl acetate (DSC 131° C.). The structure assignment was supported by NMR, mass spectroscopy and elemental analysis. Analysis calcd. for $C_{12}H_{23}NO_5$—½ $H_2O$: C, 54.04; H, 8.92; N, 5.25. Found: C, 53.97; H, 9.04; N, 5.53.

EXAMPLE 35

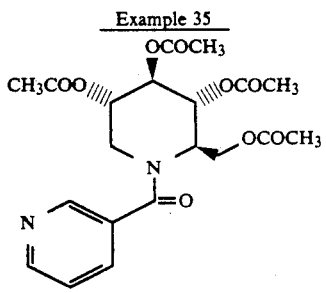

1,5-[(3-Nicotinoyl)imino]-1,5-dideoxy-D-glucitol, tetraacetate

The title compound was prepared by the Method of Example 4 by substituting nicotinoyl chloride for phenylacetyl chloride in the synthesis reaction. Structure assignment was supported by NMR.

EXAMPLE 36

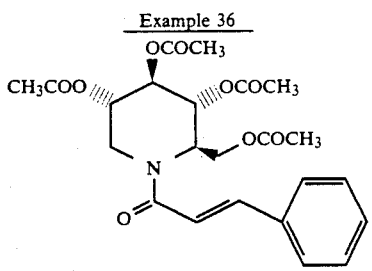

1,5-(Cinnamoylimino)-1,5-dideoxy-D-glucitol, tetraacetate

Triethylamine (0.5 ml) was added to a cold (0° C.) solution of 1,5-dideoxy-1,5-imino-D-glucitol (0.5 g, 0.0015 mole) and cinnamoyl chloride (0.25 g, 0.0015 mole) in 50 ml tetrahydrofuran. The mixture was allowed to come to room temperature and stirred for 3 days. The reaction mixture was concentrated in vacuo to an oily solid. Ethyl acetate was added to the residue and the solid removed by filtration. After concentrating the filtrate in vacuo, the title compound was purified by silica gel chromatography. The structure assignment was supported by NMR, infrared spectra and elemental analysis. Analysis calcd. for $C_{23}H_{27}NO_9$: C, 59.86; H, 5.90; N, 3.04. Found: C, 59.66; H, 5.93; N, 2.99.

EXAMPLE 37

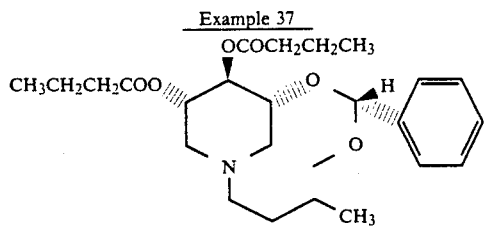

1,5-(Butylimino)-1,5-dideoxy-4R,6-O-(phenylmethylene)-D-glucitol, 2,3-dibutyrate The title compound was prepared by the Method of Example 24 by substituting butyric anhydride for acetic anhydride in the synthesis reaction. The structure assignment was supported by NMR, infrared spectra and elemental analysis. Analysis calcd. for $C_{25}H_{37}NO_6$: C, 67.09; H, 8.33; N, 3.13. Found: C, 67.05; H, 8.44; N, 3.12.

EXAMPLE 38

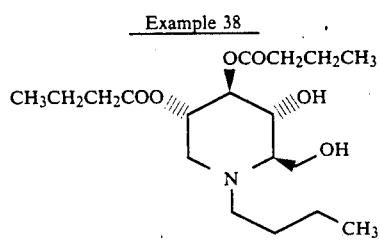

1,5-(Butylimino)-1,5-dideoxy-D-glucitol, 2,3-dibutyrate

The title compound was prepared by the Method of Example 28 by substituting the title compound of Example 37 for the title compound of Example 24. Structure assignment was supported by NMR and elemental analysis. Analysis calcd. for $C_{18}H_{33}NO_6$: C, 60.14; H, 9.25; N, 3.90. Found: C, 59.98; H, 9.38; N, 3.82.

EXAMPLE 39

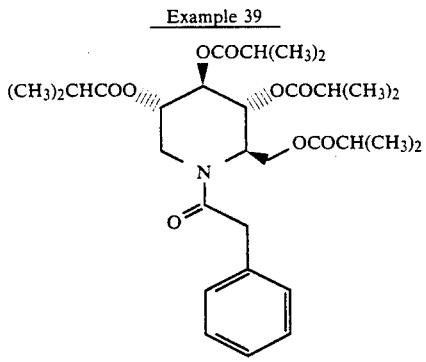

1,5-(Phenylacetylimino)-1,5-dideoxy-D-glucitol, tetraisobutyrate

The title compound was prepared by the Method of Example 4 by substituting the title product of Example 19 for the title product of Example 3 in the synthesis reaction. (DSC 96° C., from ethyl acetatehexane.) The structure assignment was supported by NMR, infrared spectra and elemental analysis. Analysis calcd. for $C_{30}H_{43}NO_9$: C, 64.15; H, 7.72; N, 2.49. Found: C, 64.15; H, 7.77; N, 2.30.

EXAMPLE 40

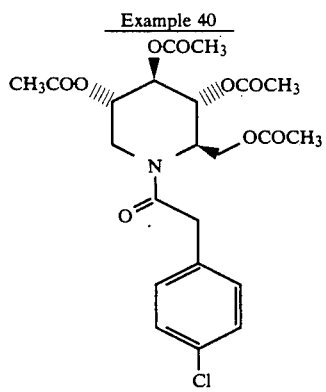

1,5-[(4-Chlorophenyl)acetylimino]-1,5-dideoxy-D-glucitol, tetraacetate

The title compound was prepared by the Method of Example 4 by substituting para-chlorophenylacetyl chloride for phenylacetyl chloride in the synthesis reaction. The structure assignment was supported by NMR, infrared spectra and elemental analysis. Analysis calcd. for $C_{22}H_{26}ClNO_9$: C, 54.61; H, 5.42; Cl, 7.33; N, 2.89. Found: C, 54.61; H, 5.45; Cl, 7.35; N, 2.88.

EXAMPLE 41

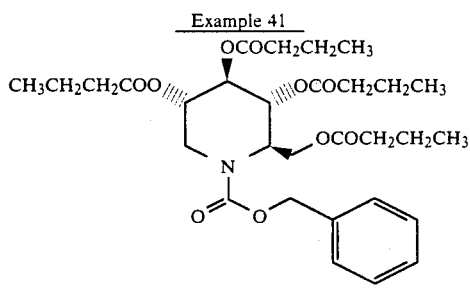

1,5-(Benzyloxycarbonylimino)-1,5-dideoxy-D-glucitol, tetrabutyrate

The title compound was prepared by the Method of Example 15 by substituting butyric anhydride for isobutyric anhydride in the synthesis reaction. The structure assignment was supported by NMR, infrared spectra and elemental analysis. Analysis calcd. for $C_{30}H_{43}NO_{10}$: C, 62.38; H, 7.50; N, 2.42. Found: C, 62.21; H, 7.52; N, 2.42.

EXAMPLE 42

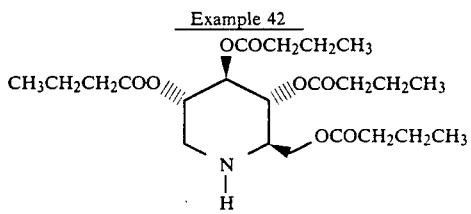

1,5-Dideoxy-1,5-imino-D-glucitol, tetrabutyrate

The title compound was prepared by the Method of Example 19 and substituting the product of Example 41 for the product of Example 15. The structure assignment was supported by NMR infrared spectra and elemental analysis. Analysis calcd. for $C_{22}H_{37}NO_8$: C, 59.58; H, 8.41; N, 3.16. Found: C, 59.46; H, 8.52; N, 3.19.

EXAMPLE 43

Various compounds as prepared above were tested for inhibition of visna virus in vitro in a plaque reduction assay as follows:

METHOD

Cell and virus propagation

Sheep choroid plexus(SCP) cells were obtained from American Type Culture Collection (ATCC) catalogue number CRL 1700 and were routinely passaged in vitro in Dulbecco's Modified Eagles (DME) medium supplemented with 20% fetal bovine serum (FBS). SCP cells were passaged once per week at a 1:2 or 1:3 split ratio. Visna was titrated by plaque assay in six-well plates. Virus pools were stored at −70° C.

Plaque reduction assay

SCP cells were cultured in 6-well plates to confluence. Wells were washed two times with serum free Minimal Essential Medium (MEM) to remove FBS. 0.2 ml of virus was added per well in MEM supplemented with 4 mM glutamine and gentamycin. After 1 hour adsorption, the virus was aspirated from each well. The appropriate concentration of each compound in 5 ml of Medium 199 (M-199) supplemented with 2% lamb serum, 4 mM glutamine, 0.5% agarose and gentamycin was added to each well. Cultures were incubated at 37° C. in a humidified 5% $CO_2$ incubator for 3-4 weeks. To terminate the test: cultures were fixed in 10% formalin, the agar removed, the monolayers stained with 1% crystal violet and plaques counted. Each compound concentration was run in triplicate. Control wells (without virus) were observed for toxicity of compounds at the termination of each test and graded morphologically from 0 to 4.0 is no toxicity observed while 4 is total lysing of the cell monolayer.

96 well plate assay

The 96 well plate assay was performed similarly to the plaque assay above with modifications. SCP cells were seeded at $1 \times 10^4$ cells per well in 0.1 ml DME medium. When confluent, the wells were washed with serum free MEM and 25 ul of virus added in M-199 supplemented with 2% lamb serum. After 1 hour, 75 uL of medium containing test compound was added to each well containing virus. After 2-3 weeks incubation the cytopathic effect of the virus was determined by staining with a vital stain. Cell viability was measured by determining stain density using a 96 well plate reader.

Control wells without virus were completed to determine the toxicity of compounds.

RESULTS

Table 1, below, sets forth the results of the assay for the compounds of Examples 3, 4, 5 and 7 compared to the N-butyl derivative of 1,5-dideoxy-1,5-imino-D-glucitol (N-Bu-DNJ) as a control standard.

TABLE 1

PLAQUE REDUCTION ASSAY

| Compound Example No. | Concentration (mM) | Toxicity | Antiviral Activity |
|---|---|---|---|
| 3 | 1.0 | 0 | A |
|   | 0.5 | 0 | A |
| 4 | 1.0 | 0 | A |
|   | 0.5 | 0 | A |
| 5 | 1.0 | 0 | A |
|   | 0.5 | 0 | A |
|   | 0.1 | 0 | A |
| 7 | 1.0 | 0 | A |
|   | 0.5 | 0 | A |
|   | 0.1 | 0 | A |
| N-Bu-DNJ | 1.0 | 2 | A |
|   | 0.1 | 1 | A |
|   | 0.01 | 0 | I |
|   | 0.001 | 0 | I |
| 8 | 1.0 | 0 | A |
|   | 0.1 | 0 | A |
| 10 | 0.125 | 3 | A |
|   | 0.0625 | 2 | A |
|   | 0.03125 | 1 | A |
| 12 | 0.03125 | 2 | A |
|   | 0.0156 | 1 | A |
|   | 0.0075 | 1 | A |
| 14 | 1.0 | 4 | Toxic |
|   | 0.1 | 2 | A |
|   | 0.01 | 0 | A |
|   | 0.001 | 0 | A |
| 16 | 1.0 | 4 | Toxic |
|   | 0.1 | 1 | A |
|   | 0.01 | 0 | A |
|   | 0.001 | 0 | A |
| 17 | 0.1 | 4 | Toxic |
|   | 0.01 | 2 | A |
| 18 | 1.0 | 0 | A |
|   | 0.1 | 1 | A |
| 20 | 1.0 | 2 | A |
|   | 0.1 | 1 | A |
|   | 0.01 | 0 | A |
| 22 | 1.0 | 0 | A |
|   | 0.1 | 0 | A |
|   | 0.01 | 0 | A |
| 24 | 1.0 | 0 | A |
| 25 | 1.0 | 2 | A |
|   | 0.1 | 1 | A |

A = active compound
I = inactive compound
Toxicity graded on 0 to 4 scale 0 = no toxicity. 4 = total cell lysates
N-Bu-DNJ = N-butyl-deoxynojirimycin used as a control standard.

The antiviral agents described herein can be used for administration to a mammalian host infected with a virus, e.g. visna virus or in vitro to the human immunodeficiency virus, by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such other examples be included within the scope of the appended claims.

What is claimed is:

1. An O-acylated derivative of 1,5-dideoxy-1,5-imino-D-glucitol containing an N-aroyl radical selected from the group consisting of phenylacetyl, benzyloxycarbonyl, biphenylacetyl, phenoxyacetyl, chlorophenylacetyl, cinnamoyl, hydrocinnamoyl and nicotinoyl, and in which from one to four of the free hydroxyl groups are acylated with carboxylic alkanoyl groups having from one to eight carbon atoms, provided that when N-aroyl is benzyloxycarbonyl, the carboxylic alkanoyl groups contain from four to eight carbon atoms.

2. An O-acylated derivative of 1,5-dideoxy-1,5-imino-D-glucitol containing an N-acyl radical selected from the group consisting of methyl malonyl and ethyl malonyl, and in which from one to four of the free hydroxyl groups are acylated with carboxylic alkanoyl groups having from one to eight carbon atoms.

3. 1,5-(Butylimino)-1,5-dideoxy-D-glucitol, tetrabutyrate.

4. 1,5-(Butylimino)-1,5-dideoxy-D-glucitol, tetraisobutyrate.

* * * * *

UNITED STATES PATENT AND TRADEMARK OFFICE
CERTIFICATE OF CORRECTION

PATENT NO. : 5,003,072

DATED : March 16, 1991

INVENTOR(S) : Richard A. Partis, Frank J. Koszyk and Richard A. Mueller

It is certified that error appears in the above-identified patent and that said Letters Patent is hereby corrected as shown below:

At col. 10, line 56, "$C_{22}$" should read --$C_{26}$--. At col. 12, lines 60-65, the dangling group at the right of the nitrogen-containing ring structure should be connected at its two left unbonded positions with bond lines to the C-4 and C-5 carbon atoms, respectively, on said ring structure similar to that as shown in the structure at col. 12, lines 40-43. At col. 13, lines 27-28, col. 15, lines 20-22, col. 15, lines 42-44, and col. 17, lines 64-65, the C-5 and C-6 carbon atoms should be connected with a single bond line similar to that as shown in the structure at col. 12, lines 40-43.

Signed and Sealed this

Twenty-sixth Day of May, 1998

*Attest:*

BRUCE LEHMAN

*Attesting Officer*   Commissioner of Patents and Trademarks